(12) United States Patent
Schattenmann

(10) Patent No.: US 6,420,585 B1
(45) Date of Patent: Jul. 16, 2002

(54) METHOD FOR MAKING TRIORGANOOXYSILANES

(75) Inventor: Florian Johannes Schattenmann, Ballston Lake, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/951,957

(22) Filed: Sep. 14, 2001

(51) Int. Cl.⁷ .............................. C07F 7/08; C07F 7/18
(52) U.S. Cl. ...................................... 556/474; 556/482
(58) Field of Search ................... 556/474, 482

(56) References Cited

U.S. PATENT DOCUMENTS 2,473,260 A    6/1949   Rochow

OTHER PUBLICATIONS

Bazant et al., "Organosilicon Compounds", vol. 2, part 1, Academic Press, NY, 1965, pp. 77, 192, and 361.*

"Five–coordinate Potassium Dihydridosilicates: Synthesis and Some Aspects of Their Reactivity", B. Becker et al. Journal of Organometallic Chemistry, 368 (1989) C–25–FC28.

"Pentacoordinate Dihydridosilicates: Synthesis, Structure, and Aspects of Their Reactivity", Robert J.P. Corriu et al., American Chemical Society (1991).

"Interaction of Tetraethoxysilane With Sodium Hydride"— A.I. Kuznetsov—1979 Plenum Publishing Corp., pp. 1732–1734.

"Pentacoordinate Hydridosilicates: Synthesis and Some Aspects of Their Reactivity", Robert J.P. Corriu et al.— Organometallics 1991, 10–pp. 2297–2303.

* cited by examiner

Primary Examiner—Paul F. Shaver
(74) Attorney, Agent, or Firm—Bernadette M. Bennett; Noreen C. Johnson

(57) ABSTRACT

A method for the preparation of triorganooxysilanes containing one silicon-hydrogen bond is provided which comprises reacting at least one tetraorganooxysilane with at least one metal hydride.

19 Claims, No Drawings

METHOD FOR MAKING TRIORGANOOXYSILANES

The government may have certain rights in this invention pursuant to contract number DE-FC02-98CH10931 awarded by the United States Department of Energy.

BACKGROUND OF THE INVENTION

The present invention relates to a method for making triorganooxysilanes. More particularly, the present invention relates to a process involving the reaction of a tetraorganooxysilane in the presence of a metal hydride.

Triorganooxysilanes are silicon-containing compounds of the formula $(RO)_3SiH$ where each R independently represents a monovalent hydrocarbon group such as an alkyl group, aryl group, aralkyl group, alkaryl group, cycloalkyl group, or bicycloalkyl group. Triorganooxysilanes, are commonly made from silicon dioxide via elemental silicon. Unfortunately, elemental silicon is manufactured from silicon dioxide by an energy intensive reduction process.

The process commonly used commercially for the production of silicones and more particularly, alkoxysilanes, was first described by Rochow et al., U.S. Pat. No. 2,473,260. The Rochow process uses silicon, also referred to as elemental silicon, as a starting material. To prepare elemental silicon, silicon dioxide must be reduced. The elemental silicon is then oxidized to yield alkoxysilanes via a reaction of the silicon with methanol in the presence of a copper catalyst. It is well known in the art that the silicon-oxygen bond in silicon dioxide is extremely stable. In order to break the silicon-oxygen bond, a large amount of energy is consumed when silicon dioxide is reduced to elemental silicon. Thus, due to the large amount of energy needed to break the silicon-oxygen bond, the synthesis of silicones from silicon dioxide using the Rochow process is expensive and not energy efficient.

In the past, the controlled synthesis of triorganooxysilanes with one silicon-hydrogen bond has relied heavily on the reduction of silicon dioxide to elemental silicon. Unfortunately, the large amount of energy needed for synthesizing silicones such as triorganooxysilanes from silicon dioxide can be problematic. Thus, new synthetic routes are constantly being sought which can form silicon-hydrogen bonds.

SUMMARY OF THE INVENTION

The present invention provides a method for the preparation of triorganooxysilanes containing at least one silicon-hydrogen bond comprising reacting at least one tetraorganooxysilane with at least one metal hydride.

DETAILED DESCRIPTION OF THE INVENTION

The present invention relates to a process involving the reaction of at least one tetraorganooxysilane and at least one metal hydride to form a triorganooxysilane containing a silicon-hydrogen bond. Tetraorganooxysilanes are of the formula $(RO)_4Si$ where each R independently represents a monovalent hydrocarbon group such as an alkyl group, aryl group, aralkyl group, alkaryl group, cycloalkyl group, or bicycloalkyl group. The term "alkyl group" is intended to designate both normal alkyl and branched alkyl groups. Normal and branched alkyl groups are preferably those containing carbon atoms in a range between about 1 and about 22, and include as illustrative non-limiting examples methyl, ethyl, propyl, isopropyl, butyl, tertiary-butyl, pentyl, neopentyl, hexyl, octyl, decyl, dodecyl. Aryl groups include an example such as phenyl. Cyclo- or bicycloalkyl groups represented are preferably those containing ring carbon atoms in a range between about 3 and about 12 with a total number of carbon atoms less than or equal to about 50. Some illustrative non-limiting examples of cycloalkyl groups include cyclobutyl, cyclopentyl, cyclohexyl, methylcyclohexyl, and cycloheptyl. Preferred aralkyl groups are those containing carbon atoms in a range between about 7 and about 14; these include, but are not limited to, benzyl, phenylbutyl, phenylpropyl, and phenylethyl. Typical tetraorganooxysilanes include tetraalkoxysilanes such as tetramethoxysilane, tetraethoxysilane, and tetraisopropoxysilane; tetraaryloxysilanes such as tetraphenoxysilane; as well as tetra(alkoxyaryloxy)silanes such as dimethoxydiphenoxysilane. Typically, the level of purity of the tetraorganooxysilane is at least about 80% by weight and preferably, about 95% by weight.

Metal hydrides include, but are not limited to, sodium hydride, lithium hydride, potassium hydride, rubidium hydride, cesium hydride, magnesium hydride, calcium hydride, strontium hydride, barium hydride, aluminum hydride, and combinations thereof. The metal hydride is preferably sodium hydride or lithium hydride. Metal hydrides also include metal borohydrides, for example, lithium borohydride, potassium borohydride and sodium borohydride.

Triorganooxysilanes are compounds of the formula $(RO)_3SiH$ where R is defined as above. Preferably, R is methyl, ethyl, or propyl.

The reaction commonly can be practiced in a fixed bed reactor. The method for preparation of triorganooxysilanes, however, can be performed in other types of reactors, such as fluid bed reactors and stirred bed reactors. More specifically, the fixed bed reactor is a column that contains the metal hydride wherein a carrier gas, such as an inert gas of nitrogen, hydrogen, or argon, is passed through at a rate in a range between about 0.1 milliliters per minute (ml/min) and about 100 ml/min and preferably, in a range between about 0.5 ml/min and about 30 ml/min. The tetraorganooxysilane is typically fed into the carrier gas stream. A stirred bed is similar to a fixed bed in which there is mechanical agitation of some sort in order to keep the bed in constant motion. A fluidized bed reactor, on the other hand, is a bed comprising metal hydride which is fluidized; that is, the metal hydride is suspended in the gas, typically argon, that is passed through the reactor. Reaction typically occurs at a temperature in a range between about 50° C. and about 600° C. and more typically, in a range between about 200° C. and about 450° C.

The reaction of the present invention can be performed in batch mode, continuous mode, or semi-continuous mode. With a batch mode reaction, for instance, all of the reactant components are combined and reacted until most of the reactants are consumed. In order to proceed, the reaction has to be stopped and additional reactant added. A fixed bed and stirred bed may both be run under batch conditions. In contrast, a fluidized reactor is typically run under continuous conditions. With continuous conditions, the reaction does not have to be stopped in order to add more reactants.

The tetraorganooxysilane is typically added to the reactor via any convenient method to provide batch, continuous, or semi-continuous means of addition. A pumping device, such as a motor driven syringe, is an example of a continuous means of addition. A motor driven syringe allows for consistent amounts of tetraorganooxysilane to be added to the reaction mixture at given time intervals. Addition of the tetraorganooxysilane via a motor driven syringe is illustrative and non-limiting. Manual injection is also a common method for the addition of tetraorganooxysilanes. Typically, the tetraorganooxysilane is added at a rate in a range between about 0.1 milliliters per hour (ml/h) and about 10 ml/h, and preferably, in a range between about 0.5 ml/h and about 2.1 ml/h. The tetraorganooxysilane is typically added in a mole ratio of metal hydride to tetraorganooxysilane in a range between about 10:1 and about 1:100 and commonly, a mole ratio of metal hydride to tetraorganooxysilane in a range between about 5:1 and 1:10. The reaction is typically at about atmospheric pressure.

Products in the triorganooxysilane synthesis may be isolated by any convenient means. Typically, product(s) may be isolated by condensation into fractions typically referred to as condensate. Products may be purified by any convenient means such as distillation. Once the fractions are collected, the formation of the triorganooxysilane may be confirmed by methods such as gas chromatography (GC), gas chromatography-mass spectroscopy (GC/MS), and proton nuclear magnetic resonance spectroscopy ($^1$H-NMR), carbon nuclear magnetic resonance spectroscopy ($^{13}$C-NMR) and silicon nuclear magnetic resonance spectroscopy ($^{29}$Si-NMR).

An important advantage of using a tetraorganooxysilane and metal hydride as starting materials for the preparation of triorganooxysilanes with one silicon-hydrogen bond is that it is energy efficient. The present invention does not require the reduction of silicon dioxide to elemental silicon.

Triorganooxysilanes obtained by the present method may be used in a wide variety of applications. For example, triorganooxysilanes may be used as precursors to silicones and organofunctional silicon compounds, precursors to pure and ultra-pure silicon dioxide, coupling agents, additives for plastic applications, and adhesion promoters.

In order that those skilled in the art will be better able to practice the invention, the following examples are given by way of illustration and not by way of limitation.

EXAMPLE 1

Sodium hydride [95% purity; 0.97 grams (g); 38.4 millimole (mmol)] was charged into a fixed bed flow reactor with vertical furnace and flushed with argon carrier gas at a rate of 14 milliliters per minute (ml/min). The initial reactor temperature was about 200° C. The reactor was heated in the presence of argon as carrier gas. Tetramethoxysilane [2.13 milliliters per hour (ml/h); 14.4 millimoles per hour (mmol/h)] was fed into the carrier gas stream using a motor driven syringe. The reactor effluent downstream was collected in fractions using a water-chilled condenser and analyzed by gas chromatography. After collecting a fraction, typically in a range between about 0.5 grams and about 2 grams, the reactor temperature was increased by 25° C. as seen in Table 1. The temperature was ramped for screening purposes. Trimethoxysilane [HSi(OMe)$_3$] formation was confirmed by gas chromatography, GC/MS and multinuclear NMR techniques. The percentages of trimethoxysilane refer to percentages of the individual samples downstream of the reactor including unreacted tetramethoxysilane. Results can be seen in Table 1.

TABLE 1

| Fraction | Weight of sample (g) | Temperature (° C.) | % HSi(OMe)$_3$ |
|---|---|---|---|
| 1 | 1.37 | 200 | 0 |
| 2 | 1.64 | 225 | 0.7 |
| 3 | 1.03 | 250 | 1.3 |
| 4 | 1.34 | 275 | 2.5 |
| 5 | 0.95 | 300 | 3.7 |
| 6 | 0.49 | 325 | 0.2 |
| 7 | 0.85 | 350 | trace |

EXAMPLE 2

The procedure of Example 1 was followed with the following modification: the carrier gas was hydrogen (14 ml/min). Results can be seen in Table 2

TABLE 2

| Fraction | Weight of sample (g) | Temperature (° C.) | % HSi(OMe)$_3$ |
|---|---|---|---|
| 1 | 1.67 | 200 | 0 |
| 2 | 0.93 | 225 | 0.6 |
| 3 | 0.96 | 250 | 3.7 |
| 4 | 1.03 | 275 | 5.5 |
| 5 | 0.96 | 300 | 6.4 |
| 6 | 1.20 | 325 | 5.8 |
| 7 | 0.60 | 350 | trace |

EXAMPLE 3

The procedure of Example 1 was followed with the following modification: the metal hydride was lithium hydride (1.14 g; 142.5 mmol). Results can be seen in Table 3.

TABLE 3

| Fraction | Weight of sample (g) | Temperature (° C.) | % HSi(OMe)$_3$ |
|---|---|---|---|
| 1 | 0.70 | 200 | 0 |
| 2 | 0.93 | 225 | 0.2 |
| 3 | 0.99 | 250 | 0.5 |
| 4 | 1.20 | 275 | 3.5 |
| 5 | 1.00 | 275 | 1.8 |
| 6 | 1.00 | 300 | 6.2 |
| 7 | 0.92 | 325 | 12.1 |
| 8 | 0.95 | 350 | 12.3 |

EXAMPLE 4

The procedure in Example 1 was used with the following modifications: the metal hydride was sodium hydride (95% purity; 1.01 g; 40.0 mmol); tramethoxysilane (1.5 ml/h; 10.2 mmol/h); the carrier gas was argon (5 ml/min). Reaction was carried out at a fixed temperature of 275° C. Results can be seen in Table 4.

TABLE 4

| Fraction | Weight of sample (g) | Temperature (° C.) | % HSi(OMe)$_3$ |
|---|---|---|---|
| 1 | 2.22 | 275 | 4.3 |
| 2 | 1.63 | 275 | 2.0 |
| 3 | 1.47 | 275 | 1.4 |

TABLE 4-continued

| Fraction | Weight of sample (g) | Temperature (° C.) | % HSi(OMe)$_3$ |
|---|---|---|---|
| 4 | 1.15 | 275 | 1.1 |
| 5 | 1.89 | 275 | 1.0 |

EXAMPLE 5

The procedure in Example 1 was used with the following modifications: the metal hydride was lithium hydride (1.5 g; 187.5 mmol); tetramethoxysilane (1.5 ml/h; 10.2 mmol/h); the carrier gas was argon (5 ml/min). Reaction was started at a temperature of 300° C. Results can be seen in Table 5.

TABLE 5

| Fraction | Weight of Sample (g) | Temperature (° C.) | % HSi(OMe)$_3$ |
|---|---|---|---|
| 1 | 1.16 | 300 | 12.4 |
| 2 | 1.37 | 325 | 12.7 |
| 3 | 1.25 | 350 | 12.1 |

EXAMPLE 6

The procedure in Example 1 was used with the following modifications: the metal hydride was sodium hydride [95% purity; 1.0 grams (g); 39.6 millimole (mmol)]; tetraethoxysilane (0.5 ml/h; 2.4 mmol/h); the carrier gas was argon (1 ml/min). Reaction was carried out at a fixed temperature of 250° C. Results of percent triethoxysilane produced (HSi(OEt)$_3$) can be seen in Table 6.

TABLE 6

| Fraction | Weight of Sample (g) | Temperature (° C.) | % HSi(OEt)$_3$ |
|---|---|---|---|
| 1 | 1.36 | 250 | 2.3 |
| 2 | 1.50 | 250 | 2.1 |
| 3 | 1.34 | 250 | 1.9 |
| 4 | 1.66 | 250 | 2.0 |

EXAMPLE 7

The procedure in Example 1 was used with the following modifications: tetra-n-propoxysilane (1.5 mL/h; 5.2 mmol/h); the carrier gas was nitrogen (5 mL/min). The reaction was carried out at a fixed temperature of 250° C. results of percent tripropoxysilane produced (HSi(O-n-Pr)$_3$) can be seen in Table 7.

TABLE 7

| Fraction | Weight of Sample (g) | Temperature (° C.) | % HSi(O-n-Pr)$_3$ |
|---|---|---|---|
| 1 | 1.10 | 250 | 3.2 |
| 2 | 1.24 | 250 | 1.8 |
| 3 | 1.93 | 250 | 1.3 |
| 4 | 1.74 | 250 | 1.0 |

While typical embodiments have been set forth for the purpose of illustration, the foregoing description should not be deemed to be a limitation on the scope of the invention. Accordingly, various modifications, adaptations, and alternative may occur to one skilled in the art without departing from the spirit and scope of the present invention.

What is claimed is:

1. A method for the preparation of triorganooxysilanes containing one silicon-hydrogen bond comprising reacting at least one tetraorganooxysilane with at least one metal hydride.

2. The method according to claim 1, wherein the tetraorganooxysilane comprises tetraalkoxysilanes, tetraaryloxysilanes, tetra(alkoxyaryloxy)silanes, or combinations thereof.

3. The method according to claim 2, wherein the tetraorganooxysilane comprises tetramethoxysilane.

4. The method according to claim 2, wherein the tetraorganooxysilane comprises tetraethoxysilane.

5. The method according to claim 2, wherein the tetraorganooxysilane comprises tetrapropoxysilane.

6. The method according to claim 1, wherein the metal hydride is selected from the group consisting of sodium hydride, lithium hydride, potassium hydride, rubidium hydride, cesium hydride, magnesium hydride, calcium hydride, strontium hydride, barium hydride, aluminum hydride, sodium borohydride, lithium borohydride, potassium borohydzide, and combinations thereof.

7. The method according to claim 6, wherein the metal hydride comprises sodium hydride.

8. The method according to claim 6, wherein the metal hydride comprises lithium hydride.

9. The method according to claim 1, wherein the reaction occurs in a reactor bed which comprises a reactor selected from the group consisting of a fixed bed reactor, a fluidized bed reactor and a stirred bed reactor.

10. The method according to claim 9, wherein the reaction occurs in a fixed bed reactor.

11. The method according to claim 9, wherein the reaction is operated in batch mode.

12. The method according to claim 9, wherein the reaction is operated in continuous mode.

13. The method according to claim 1, wherein the reaction is conducted at a temperature in a range between about 50° C. and about 600° C.

14. The method according to claim 13, wherein the reaction is conducted at a temperature in a range between about 200° C. and about 450° C.

15. The method according to claim 1, wherein the metal hydride is present in a mole ratio of hydride to tetraorganooxysilane in a range between about 10:1 and about 1:100.

16. The method according to claim 15, wherein the metal hydride is present in a mole ratio of hydride to tetraorganooxysilane in a range between about 5:1 and about 1:10.

17. A method for the preparation of trimethoxysilane containing one silicon-hydrogen bond comprising reacting tetramethoxysilane with sodium hydride wherein the sodium hydride is present in a mole ratio of hydride to tetramethoxysilane in a range between about 5:1 and about 1:10.

18. A method for the preparation of triethoxysilane containing one silicon-hydrogen bond comprising reacting tetraethoxysilane with sodium hydride wherein the sodium hydride is present in a mole ratio of hydride to tetraethoxysilane in a range between about 5:1 and about 1:10.

19. A method for the preparation of tripropoxysilane containing one silicon-hydrogen bond comprising reacting tetrapropoxysilane with sodium hydride wherein the sodium hydride is present in a mole ratio of hydride to tetrapropoxysilane in a range between about 5:1 and about 1:10.

* * * * *